(12) United States Patent
Hamamoto et al.

(10) Patent No.: US 6,676,808 B2
(45) Date of Patent: Jan. 13, 2004

(54) METHOD FOR STARTING UP DISTILLING COLUMN

(75) Inventors: Kei Hamamoto, Himeji (JP); Yukihiro Matsumoto, Kobe (JP); Sei Nakahara, Himeji (JP); Misao Inada, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 90 days.

(21) Appl. No.: 09/871,213

(22) Filed: May 31, 2001

(65) Prior Publication Data
US 2002/0008010 A1 Jan. 24, 2002

(30) Foreign Application Priority Data
Jun. 2, 2000 (JP) ........................................ 2000-166389

(51) Int. Cl.[7] .............................. B01D 3/34; B01D 3/42; C07C 51/44
(52) U.S. Cl. ...................... 203/8; 203/2; 203/3; 203/49; 203/98; 203/DIG. 7; 203/DIG. 21; 562/600
(58) Field of Search .................. 203/8, 9, 2, 3, 203/49, 98, DIG. 7, DIG. 21; 562/600

(56) References Cited

U.S. PATENT DOCUMENTS

| | | | | |
|---|---|---|---|---|
| 4,061,545 A | * | 12/1977 | Watson | 203/49 |
| 4,260,821 A | * | 4/1981 | Benjamin | 203/49 |
| 4,341,600 A | * | 7/1982 | Watson | 203/56 |
| 4,365,081 A | * | 12/1982 | Shimizu et al. | 202/182 |
| 4,369,097 A | * | 1/1983 | Nezu et al. | 202/184 |
| 4,986,884 A | * | 1/1991 | Arlt et al. | 159/DIG. 16 |
| 6,348,135 B1 | * | 2/2002 | Nakahara et al. | 203/49 |

FOREIGN PATENT DOCUMENTS

GB     1265738     * 3/1972

OTHER PUBLICATIONS

Kister, H. Distillation Operation, McGraw–Hill, 1990, Chapter 12, —pp. 313–315.
Yamaguchi, T. Operating Manual of Chemica Apparatus, Nikkan Kogyo Shimbun, 1969 pp. 1–2.

* cited by examiner

Primary Examiner—Virginia Manoharan
(74) Attorney, Agent, or Firm—Mathews, Collins, Shepherd & McKay, P.A.

(57) ABSTRACT

A method for starting up a distilling column destined to handle an easily polymerizing compound-containing solution characterized by supplying at the start of the operation of the distilling column a polymerization inhibitor to the bottom liquid of the distilling column having a temperature of not higher than 80° C. Further, by supplying a reflux liquid through the top of the distilling column or the middle stage of the column prior to the start of the temperature elevation of the distilling column, thereby preventing the polymerization of the easily polymerizing compound more effectively.

6 Claims, 5 Drawing Sheets

METHOD FOR STARTING UP DISTILLING COLUMN

BACKGROUND OF THE INVENTION

1. Field of the Invention

This invention relates to a method for starting up a distilling column which is fated to handle a solution containing an easily polymerizing compound, and more particularly to a method for starting up a distilling column which supplies a polymerization inhibitor to the bottom liquid of the column in a state prior to the stationary state, thereby preventing the column itself and the devices attached thereto from developing polymerization and clogging, and securing safety of itself as well.

2. Description of Related Art

Such easily polymerizing compounds as acrylic acid and methacrylic acid are raw materials for the manufacture of commercial products and are chemical substances which are produced in large quantities at plants of a large scale. In the case of (meth)acrylic acid, for example, this easily polymerizing compound is produced by the reaction of catalytic gas phase oxidation of propylene, isobutylene, t-butanol, methyl-t-butyl ether, or acrolein. In the reaction gas obtained by the reaction of catalytic gas phase oxidation mentioned above, the (meth)acrylic acid as the target product remains mixed with other by-products. For example, the reaction mentioned above mainly generates non-condensable gases, namely unreacted propylene and acrolein, low-boiling organic compounds having lower boiling points than acrylic acid, namely steam and unreacted acrolein, impurities such as formaldehyde and acetic acid which are formed by a secondary reaction, high-boiling compounds having higher boiling points than acrylic acid, namely maleic anhydride, furfural, benzaldehyde, benzoic acid, and acrylic acid dimer, and the like. For the purpose of obtaining the target product by refining this reaction gas, therefore, it is customary to extract the product by counterflow washing the reaction gas with water or a heavy solvent and then supply the extracted product to a distilling column and refine it therein.

Since the distilling column contains therein the target product, solvent, generated gas, etc. in a mixed state, however, it has a high possibility of entailing combustion and explosion and causing the attached devices to sustain breakage. Particularly, the distilling column which handles an easily polymerizing compound further aggravates this possibility because it contains a multiplicity of components and suffers the composition in the column to vary every moment from the time the column starts its operation to the time the column reaches the stationary state. Further, when the target product is an easily polymerizing compound, it is liable to generate a polymer because of the physical properties of its own. When a gas containing molecular oxygen is supplied to the column with a view to preventing this generation of the polymer, the possibility of the supplied gas inducing explosion is heightened.

The starting method which is usually resorted to with a view to preventing such harmful effects will be explained below with reference to FIG. 5. First, for the purpose of preventing a distilling column (1) from explosion, an inert gas is supplied into the interior of the distilling column (1) through the top thereof or the bottom thereof till the entrapped air is displaced with the inert gas and the water entrapped in the column is removed in consequence of the displacement with the inert gas. Then, the initial liquid is introduced into the distilling column via a feed orifice (2) and a reboiler (3) connected to the bottom of the distilling column (1) is heated to start temperature elevation. As the temperature of the bottom liquid is elevated in consequence of this temperature elevation, the low boiling substance, easily polymerizing compound, and high boiling substance are sequentially gasified through the surface of the liquid in the order mentioned. Then, by the temperature elevation, the distillate to a condenser (4) attached to the distilling column (1) is started and the total reflux operation is carried out via a pump (6) by increasing the load to the set amount of reflux by distillate. After the total reflux operation has been stabilized and has been confirmed to bring no adverse effect on the temperature and the pressure inside the column, the supply of a gas containing molecular oxygen to the reboiler (3) is started and, at the same time, the supply of the raw material liquid to the interior of the distilling column (1) is started. Then, the distillate from the condenser (4) attached to the top part of the distilling column is started when the amount of the distillate has increased and the extraction of the bottom liquid is started after the temperature of the bottoms has risen past the present level. Part of the expelled liquid may be circulated via a pump (5) to the distilling column. After the amount supplied has reached the total set level, the stationary operation is started. During the course of this process, the operation is shifted to the stationary status simultaneously with the work of checking the generation and effect of the thermal stress by expansion due to introduction and circulation of the liquid for starting operation, checking the leakage due to application of pressure, checking the heating devices for operation, checking measuring devices for operation, and adjusting the raw materials at the time of charging the reaction vessel of the raw materials.

When the conventional method is adopted for starting up the distilling column and the target for purification happens to be such an easily polymerizing compound as (meth) acrylic acid, the reboiler, the condenser, and the wall and the bottom part of the distilling column are liable to generate a polymer during the course of temperature elevation. When this polymer adheres to the interior of a strainer in the extracting pump stemmed from the bottom part of the column, the adhering polymer has the possibility of giving rise to cavitation and bringing the pump to a stop and preventing the distilling column from continuing a safe operation.

The adhesion of the polymer to the strainer and the clogging of the strainer with the adhering polymer result in requiring the strainer to be given a cleaning work. Owing to the chemical stimulations caused by the raw material for the reaction, the product of the reaction, and the by-products and the physical hindrances caused by the adhesion of a polymer, this cleaning work imparts spiritual displeasure to the workers and compels the workers to suffer adverse effects on health. Further, the organic solvent to be used for distillation entails the problem of jeopardizing the safety of operation on account of the inflammability of the solvent. It is generally difficult to discard manually the spent organic solvent, with the size of the device to be used for cleaning and the size of the distilling column itself to be cleaned as contributory factors.

Moreover, the distilling column of this nature demands a meticulous care and calls for due time and labor when it is started up as well as it is stopped. When the polymer adheres to the distilling column during the operation of starting up the distilling column, since this polymer persists even during the course of the stationary operation of the column, it forms the core of polymerization, gradually accumulates, tends to induce further polymerization and clogging, and forms the cause to stop the continuous operation. When the operation of the distilling column and the operation of the device attached to the column are stopped because of the generation of the polymer, however, the stop of the operation of the large plant and the restart of this operation call for much time and labor. Even the partial stop of the device entails the necessity for adjusting the series of reaction conditions, with the result that the purpose of the quantity production aimed at will not be fulfilled because of the decrease in the productivity.

Further, the removal of the polymer requires to use a large amount of a solvent for detergence. When the spent solvent is discarded or disposed of as by combustion, for example, this disposal entails generation of carbon dioxide, pollution of a nearby river or coast, and failure to attain environmental protection.

When the molecular oxygen-containing gas is supplied prior to or simultaneously with the supply of a heat source for the purpose of precluding the polymerization of an easily polymerizing compound, the gas composition in the column has the possibility of inducing explosion or combustion because it falls in the explosion limits, with the result that instability will be further promoted because of the variation in the composition of the raw materials to be supplied within the interior of the distilling column and the safe start of the column will be rendered more difficult.

Further, even when the polymerization inhibitor is used in the liquid raw material to be supplied for the purpose of precluding the polymerization or the clogging caused by an easily polymerizing compound, since the vapor of the easily polymerizing compound to be generated in consequence of temperature elevation contains no polymerization inhibitor of a high boiling point, no fully effective prevention of the polymerization is attained because the polymerization tends to be induced by the condensation of the easily polymerizing compound.

SUMMARY OF THE INVENTION

The present inventor, as a result of an elaborate study concerning the state of a distilling column at the time of starting up the operation thereof, has found that the polymerization and the clogging of an easily polymerizing compound can be precluded by effecting the supply of a polymerization inhibitor to the initial liquid before the arrival of the operation at the stationary state and supplying the molecular oxygen-containing gas and the initial liquid to the prescribed site. This invention has been perfected as a result. To be specific, the tasks imposed on this invention as described above are accomplished by the following method.

A method for starting up a distilling column to handle an easily polymerizing compound-containing solution, characterized by supplying at the start of the operation of the distilling column a polymerization inhibitor to the bottom liquid of the distilling column having a temperature of not higher than 80° C.

According to this invention, by supplying the polymerization inhibitor to the bottom liquid of the distilling column having a temperature of not higher than 80° C. in starting the operation of the distilling column to handle an easily polymerizing compound-containing solution, it is made possible to preclude the polymerization of the easily polymerizing substance. Particularly when there flux liquid is supplied from the top of the distilling column or from the middle stage of the column before the temperature elevation of the distilling column is started, the polymerization of the easily polymerizing substance can be prevented more effectively because the inner wall of the column is filled with the reflux liquid. Further, by supplying an inert gas and/or the molecular oxygen-containing gas to the interior of the column till the molecular oxygen-containing gas concentration in the column reaches a level in the range of 0.1–9 vol. % before the start of the temperature elevation of the distilling column and then, during the course of the subsequent temperature elevation, supplying the molecular oxygen-containing gas in such a rate that the easily polymerizing compound gas composition within the column exceeds the upper explosion limits, the method for starting up the column is enabled to preclude the occurrence of the polymer of the easily polymerizing compounds within the distilling column and prevent the polymer from adhering to the column and causing clogging and, at the same time, prevent the interior of the distilling column from falling in the explosion limits, and enjoy safe operation.

DETAILED DESCRIPTION OF THE PREFERRED EMBODIMENTS

Figure 1:
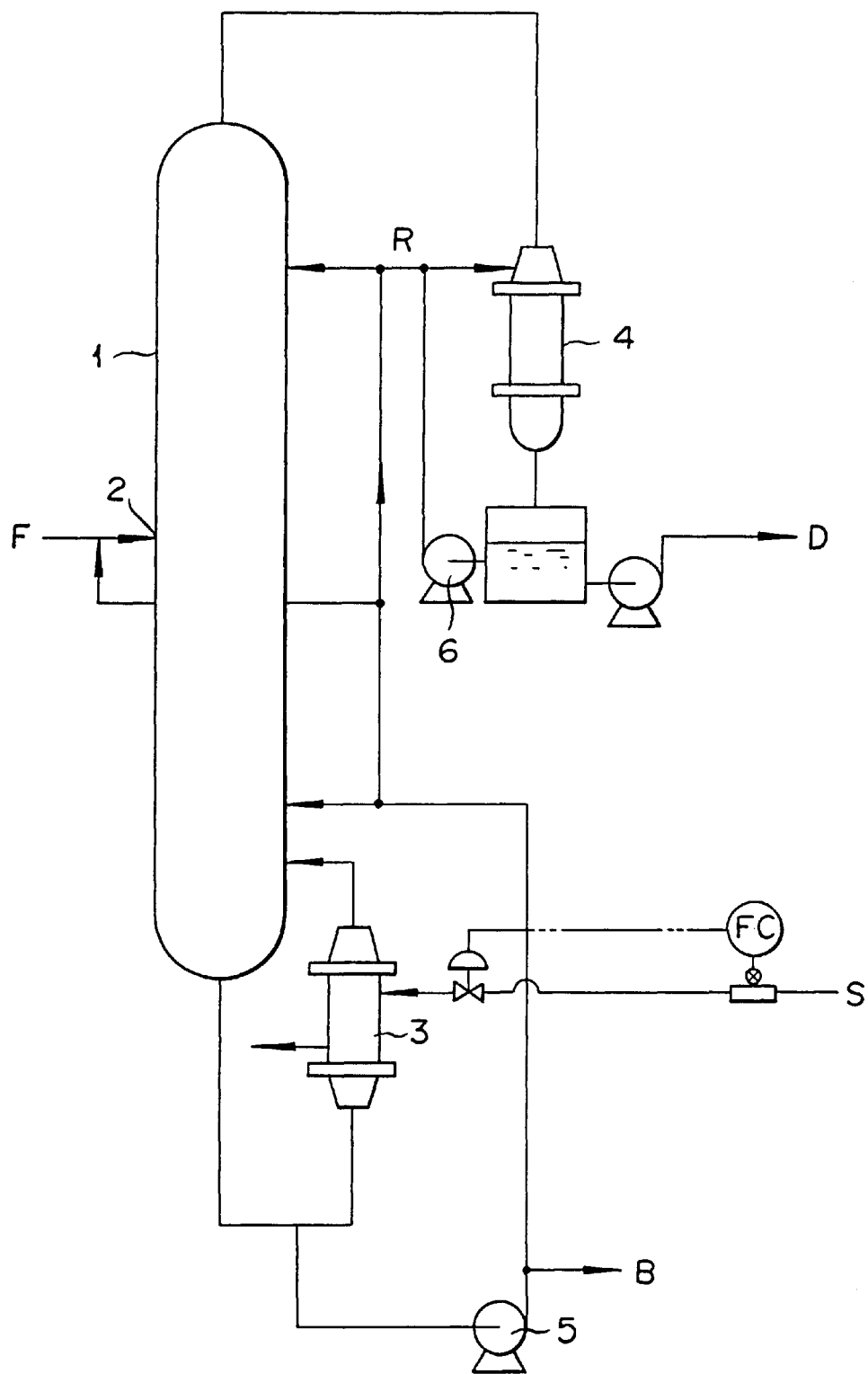
FIG. 1 is a diagram illustrating the flow of a liquid during the operation of starting up the distilling column according to this invention when the distillation is implemented by the use of an azeotropic solvent. With reference to the diagram, 1 stands for a distilling column, 2 for a raw material feed orifice, 3 for a reboiler, 4 for a condenser, 5 and 6 each for a pump, F for a raw material liquid, R for a reflux liquid, D for distillate, S for steam, and B for a bottom liquid of the column.

The first aspect of this invention consists in a method for starting up a distilling column to handle an easily polymerizing compound-containing solution, characterized by supplying at the start of the operation of the distilling column a polymerization inhibitor to the bottom liquid of the distilling column having a temperature of not higher than 80° C.

Generally, when the distilling column is set operating, it is charged in advance with a prescribed amount of feed material as an initial liquid and then allowed to undergo temperature elevation. The polymerization inhibitor is a compound which is added to the distilling column fated to handle an easily polymerizing compound-containing solution while the column is in the course of stationary operation. This polymerization inhibitor, when used solely, is incapable of accomplishing sufficient prevention of the polymerization because it generally has a high boiling point and fails to persist within the atmosphere in the distilling column after temperature elevation or prevent polymerization of an easily polymerizing compound from existing in a gaseous state. Further, the polymerization inhibitor itself has a high price and the incorporation thereof in the bottom liquid of the distilling column necessitates an extra work of preparing a solution containing this polymerization inhibitor and then feeding this solution into the feed liquid. Thus, it has been heretofore customary for the initial liquid to avoid incorporating the polymerization inhibitor therein and the polymerization inhibitor concentration in the bottom liquid of the column to remain always at a lower level then during the stationary operation of the column between the time the temperature elevation is started and the time the stationary state is assumed. In accordance with the present invention, since the polymerization inhibitor is used in the bottom liquid of the distilling column having a temperature of not higher than 80° C., the generation of a polymer in the interior of the distilling column, the condenser, and the pump attached to the reboiler or the clogging of such devices with the formed polymer can be prevented. As a result of this prevention, the increase of the boiling point of the bottom liquid of the column can be prevented due to prevention of the generation of the polymer and, particularly during the operation of starting up in which the solution composition and the gas composition are so varied that the stable operation of distillation is not easily obtained, such accidents as explosion and bumping can be prevented to ensure the safety of the operation of starting up the distilling column. Now, this invention will be described in detail below.

The distilling column which is targeted at by the present invention embraces all the distilling columns that are fated to handle an easily polymerizing compound-containing solution. The question whether it has the designation of a distilling column or not is irrelevant for this invention. Those which have been heretofore designated variously as dehydrating column, low boiling component separating column, high boiling component separating column, and azeotropic separating column are invariably applicable to this invention so long as the target solution which is fed to the relevant distilling column is an easily polymerizing compound-containing solution. Then, the term "easily polymerizing compound-containing solution" only requires to contain an easily polymerizing compound. The concentration of the solution and the question whether or not the solvent for the solution is an organic solvent or an aqueous solvent are all irrelevant for the present invention.

As concrete examples of the easily polymerizing compound, such carboxylic acids as acrylic acid, methacrylic acid, fumaric acid, and maleic acid which have an unsaturated double bond and esters of such carboxylic acids may be cited. The hydroxyl group-containing compounds which form esters with such carboxylic acids are possessed of an unsaturated double bond and are preferred to be lower aliphatic alcohols or lower alicyclic alcohols having 1–12 carbon atoms. As concrete examples of the hydroxyl group-containing compound, various alcohols such as methanol, ethanol, n-butanol, isobutanol, sec-butanol, t-butanol, 1-pentanol, 2-pentanol, 3-pentanol, cyclopentanol, 1-hexanol, 2-hexanol, 3-hexanol, cyclohexanol, 1-heptanol, 2-heptanol, 3-heptanol, 1-octanol, isooctanol, 2-ethylhexanol, isononyl alcohol, and lauryl alcohol may be cited. These alcohols may be in the form of a linear chain or in the form of a branched chain. These alcohols may be used either singly or in the form of a combination of two or more members.

As concrete examples of the solvent for containing such an easily polymerizing compound, the middle oil fraction from the distillation of a paraffin, diphenyl ether, diphenyl, and mixtures of the liquids mentioned above such as, for example, the mixture of 70–75 wt. % of diphenyl ether and 25–30 wt. % of diphenyl, and the mixture of 70–75 wt. % of diphenyl ether and 25–30 wt. % of diphenyl and blended mixture of the mixture and 0.1–25 wt. % of o-diphenyl phthalate based on the total weight of the mixture may be cited in addition to water and organic acid-containing water.

The separation of the solvent such as, for example, water or a low boiling impurity which contains the easily polymerizing compound is generally accomplished by distillation using an azeotropic solvent. Specifically, this separation is implemented by distilling through the top of an azeotropic separating column an azeotropic mixture of water and the solvent and recovering acrylic acid from the bottom of the column. As concrete example soft heazeotropic solvent, solvents containing at least one member selected from the group consisting of heptane, dimethyl cyclohexane, ethyl cyclohexane, toluene, ethylene benzene, chlorobenzene, xylene, and mixtures thereof;

solvents containing at least one member selected from the group consisting of diethyl ketone, diisopropyl ketone, methyl propyl ketone, methyl isobutyl ketone, methyl-t-butyl ketone, n-propyl acetate, n-butyl acetate, ethyl acrylate, methyl methacrylate, ethyl methacrylate, vinyl acrylate, n-propyl acrylate, allyl acetate, isopropenyl acetate, vinyl propionate, propyl propionate, methyl crotonate, methyl valerate, ethyl acetate, methyl acrylate, dibutyl ether, and mixtures thereof; and mixtures of the solvent containing at least one member selected from the group consisting of heptane, dimethyl cyclohexane, ethyl cyclohexane, toluene, ethylene benzene, chlorobenzene, xylene, and mixtures thereof and the solvent containing at least one member selected from the group consisting of diethyl ketone, diosopropyl ketone, methyl propyl ketone, methyl isobutyl ketone, methyl-t-butyl ketone, n-propyl acetate, n-butyl acetate, ethyl acrylate, methyl methacrylate, ethyl methacrylate, vinyl acrylate, n-propyl acrylate, allyl acetate, isopropenyl acetate, vinyl propionate, propyl propionate, methyl crotonate, methyl valerate, ethyl acetate, methyl acrylate, dibutyl ether, and mixtures thereof may be cited.

This invention is characterized by supplying the polymerization inhibitor to the bottom liquid of the distilling column having a temperature of not higher than 80° C. As regards the method for effecting this incorporation of the polymerization inhibitor, the incorporation may be attained by directly introducing the polymerization inhibitor into the distilling column by injecting the inhibitor into the initial liquid which has been placed in advance in the bottom of the distilling column, by charging the distilling column with the initial liquid having the polymerization inhibitor contained therein in advance, or by dissolving the polymerization inhibitor in a reflux liquid or some other solvent and introducing the resultant solution via a feed line. Further as for the method for charge of the initial liquid into the distilling column, the initial liquid may be introduced into the column from the top of the column via the condenser attached to the column as well as charged form the feed orifice of the distilling column during the normal operation.

This invention does not need to impose any particular limit on the amount of the polymerization inhibitor to be injected into the bottom liquid of the distilling column. Properly, this amount is such that the concentration of the polymerization inhibitor in the bottom liquid of the column having a temperature of not higher than 80° C. is equal to or more than the concentration in the stationary state, preferably 1 to 2 times the concentration in the stationary state, and particularly preferably 1–1.5 times the concentration in the stationary state. The concentration of the polymerization inhibitor in the stationary state, however, cannot be defined impartially because it is varies with the specific composition of the easily polymerizing compound-containing solution and the operating conditions for the other steps continuing from the distilling step such as, for example, the chemical quality, concentration, and distilling temperature of the easily polymerizing compound. Since it has been heretofore normal to start the temperature elevation of the distilling column while the polymerization inhibitor is not contained at all in the bottom liquid of the column, the polymerization inhibitor necessary for sufficient prevention of the polymerization has not been reached even by supplying the easily polymerizing compound-containing solution containing the polymerization inhibitor at a prescribed concentration after the assumption of the stationary state, namely after completion of the temperature elevation of the distilling column. By adding the polymerization inhibitor to the bottom liquid of the column having a temperature of not higher than 80° C., therefore, it is made possible to prevent the polymerization infallibly as compared with the conventional method, prevent the bottom liquid of the column from succuming to the temperature elevation due to the generation of a polymer and consequently secure safety of the operation, and accomplish a decrease in the energy for the distillation.

The polymerization inhibitor which is usable herein may be properly selected from among such compounds as hydroquinone, methoxy hydroquinone, hydroquinone monomethyl ether, cresol, phenol, t-butyl catechol, diphenyl amine, phenothiazine, and methylene blue, from among such copper chloride compounds as copper dimethyl dithiocarbamate, copper diethyl dithiocarbamate, copper dibutyl dithiocarbamate, and copper salicylate and such manganese chloride compounds as manganese acetate, from among such p-phenylene diamines as p-phenylene diamine, such N-oxyl compounds as 4-hydroxy-2,2,6,6-tetramethyl piperidinooxyl, such ureas as urea, and such thioureas as thiourea. The compounds enumerated above may be used either singly or in the form of a combination of two or more members.

Further, in this invention, it is commendable to supply a reflux liquid through the top of the distillation column or through the middle stage of the column at the same time that the polymerization inhibitor is used and prior to the start of the temperature elevation of the distilling column. It has been heretofore customary to start the temperature elevation after the distilling column has been charged with the bottom liquid. This method, however, suffers the easily polymerizing compound to gasify before the vapor of the solvent is generated so much inside the distilling column as to wet the inner wall of the column with the solvent. As a result, the gas of the easily polymerizing compound tends to adhere to the inner wall of the distilling column, then aggregate into an adhering liquid, and eventually generate a polymer. This invention, therefore, contemplates preventing the aggregation of the easily polymerizing compound and repressing the generation of the polymer by supplying the reflux liquid through the top of the distilling column prior to the temperature elevation and consequently wetting the interior of the distilling column. As the reflux liquid, not only the solvent used for the easily polymerizing compound-containing solution may be used in its unmodified form but also the bottom liquid of the column may be used. Incidentally, the reflux liquid may be supplied through the top of the column or through the middle stage of the column by means of a feed line which is provided for the distilling column or it may be supplied through the medium of a condenser which is connected to the distilling column. When the condenser forms this intermediate, the reflux liquid is supplied into the interior of the column via the site which is used for circulating the reflux liquid from the condenser.

In this invention, it is commendable to supply an inert gas and/or a molecular oxygen-containing gas into the interior of the column simultaneously with the addition of the polymerization inhibitor mentioned above or simultaneously with the supply of the reflux liquid mentioned above and prior to the start of the temperature elevation of the distilling column till the molecular oxygen-containing gas concentration within the column reaches a level in the range of 0.1–9 vol. % and then, during the temperature elevation, supply the molecular oxygen-containing gas so that the easily polymerizing compound containing gas concentration in the column can not fall in the range of exceeding the upper explosion limits. If the molecular oxygen-containing gas concentration in the interior of the column exceeds 9 vol. % (the explosion limits), the gas will have the possibility of forming an explosive mixed gas and inducing an explosion when the static electricity, for example, emits a spark. It has been heretofore customary, therefore, to suspend the supply during the course of temperature elevation in which the composition inside the column is not stable and start the supply after the composition has reached a stationary state. This practice coincides with the conventional technique which regards the operation of displacing the air or an oxygen gas entrapped in the column with an inert gas as an essential requirement for the purpose of avoiding the explosion. As a result of an elaborate study pursued concerning the relation between the molecular oxygen-containing gas concentration and the easily polymerizing compound concentration, the relation illustrated in FIG. 2 has been found. Incidentally, the expression "prior to the start of the temperature elevation" as used herein embraces the rise of the temperature of the bottom part of the column within 20° C. relative to the ambient temperature even when the heater for the temperature elevation has been put to operation.

Figure 2:
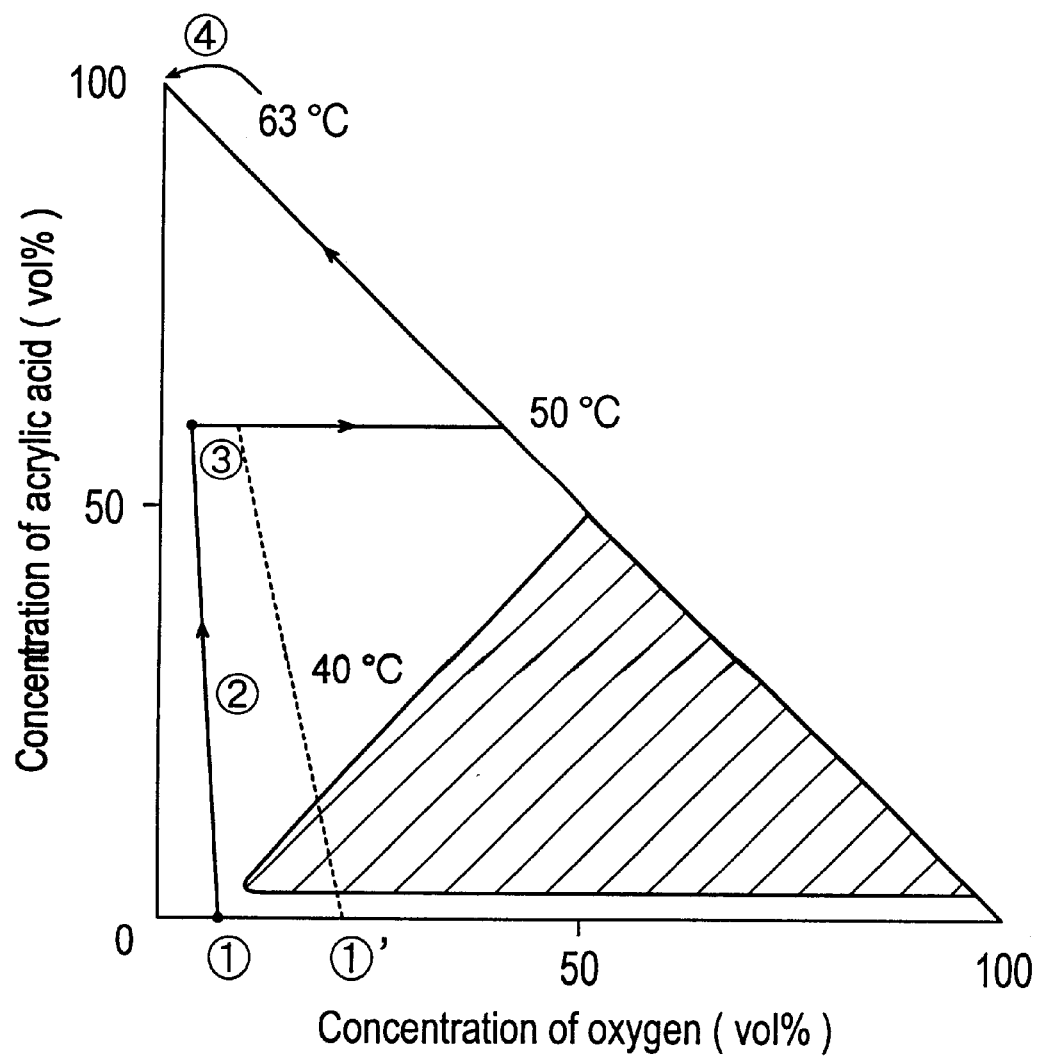
FIG. 2 is a diagram illustrating explosion limits covering the relation between concentration of acrylic acid and a molecular oxygen-containing gas in the distilling column during the distillation of acrylic acid. In the diagram, the area covered with oblique lines represents explosion limits.

FIG. 2 illustrates the percentage composition of the gas formed of acrylic acid and oxygen in the top of the distilling column. In FIG. 2, the horizontal axis forms the scale for oxygen concentration and the vertical axis form the scale for acrylic acid concentration and the part indicated with oblique lines represent explosion limits. The loci of the change in the percentage composition of the gas of acrylic acid and oxygen which are described when the pressure and the temperature inside the column are changed during an ordinary process of distillation of an easily polymerizing compound are indicated with a continuous line and a dotted line representing varying oxygen concentrations. The loci of composition will be described below. First, the acrylic acid which is supplied to the interior of the column prior to distillation is in a liquid state at normal room temperature. When a molecular oxygen-containing gas having an oxygen concentration of 21 vol. %, for example, is supplied to the interior of the column before the temperature inside the column is elevated, the gas composition in the top part of the column occupies the position of ①' in FIG. 2, namely the position having an oxygen concentration of 21 vol. % and an acrylic acid concentration of 0 vol. %. When the pressure in the top of the column is decreased from 1013 hPa to 47 hPa and the temperature in the column is elevated continuously for the sake of the distillation, since the acrylic acid in the bottom of the column is gasified, the acrylic acid concentration in the top part of the column is increased and the composition ratio of the two compounds is shifted along the dotted line. The lowest oxygen concentration in the explosion limits is taken as the limiting oxygen concentration. In FIG. 2, the limiting oxygen concentration is 9.5 vol. %.

It is noted from FIG. 2 that where the acrylic acid concentration is 3 vol. %, the oxygen concentration exceeds 9.5 vol. % and enters the explosion limits. Thus, it has been heretofore customary to prohibit completely the supply of an inert gas and/or a molecular oxygen-containing gas, let alone in a concentration of 9.5 vol. %, prior to the temperature elevation. An elaborate study of the explosion limits, however, reveals that in consequence of the increase of the concentration of the easily polymerizing compound, the oxygen concentration belonging to the explosion limits gradually decreases thereafter. By lowering the oxygen concentration at the time of starting the operation to a level below the explosion limits and supplying the molecular oxygen-containing gas during the course of the temperature elevation so as to avoid the explosion limits, it is made possible to prevent the polymerization and secure the safety of the operation as well. When the focus indicated with the dotted line in FIG. 2 is faithfully followed, the polymerization can be prevented. Since the focus crosses the explosion limits, however, the operation of starting up the distilling column is evidently destitute safety of operation.

Figure 3:
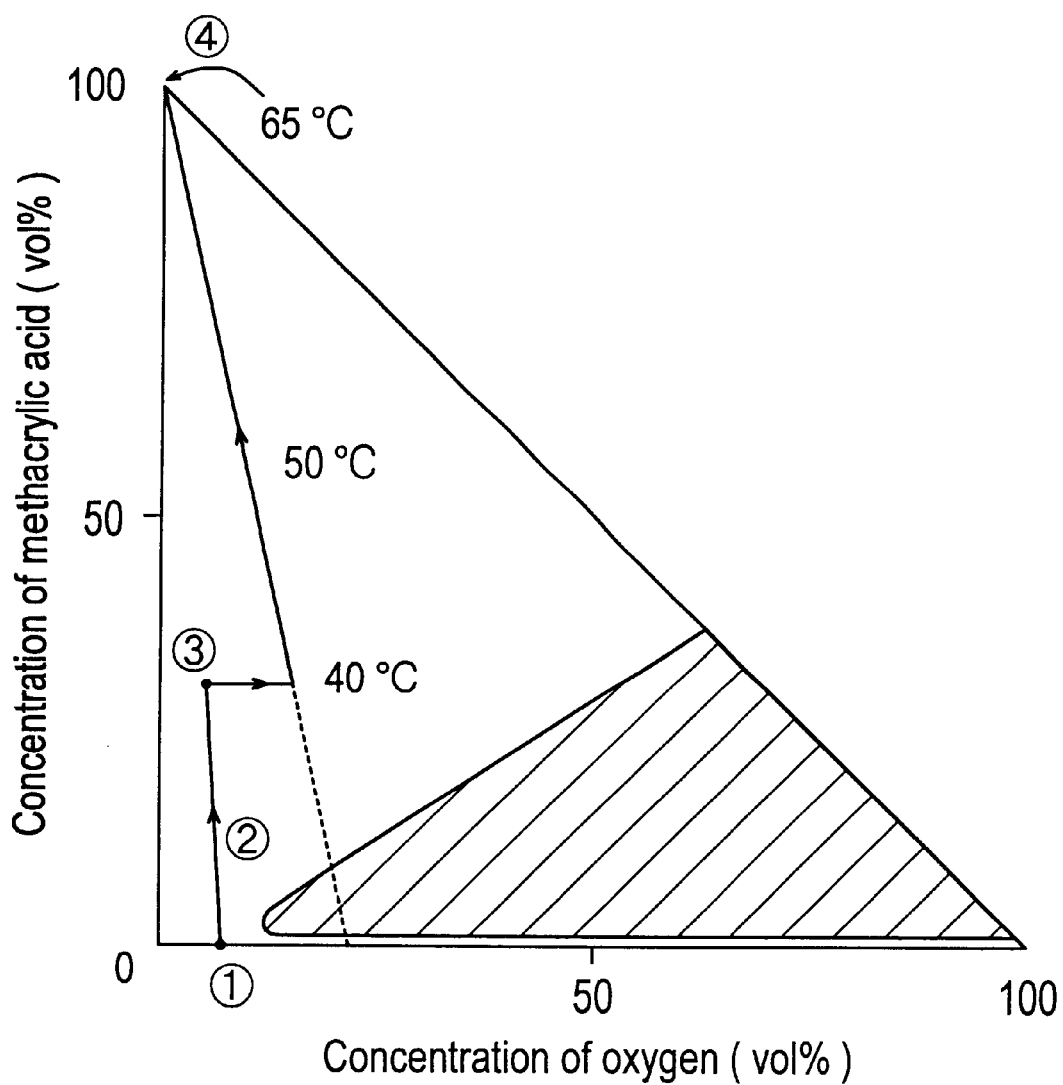
FIG. 3 is a diagram illustrating explosion limits covering the relation between concentration of methacrylic acid and a molecular oxygen-containing gas in the distilling column during the distillation of methacrylic acid. In the diagram, the area covered with oblique lines represents explosion limits.

This invention sets the upper limit of the oxygen concentration at 9 vol. %. The reason for adopting this upper limit is that in the operation of distilling an easily polymerizing compound, the change in the solution composition occurring between the time the temperature elevation of the distilling column begins and the time the distillation reaches the stationary state has no possibility of actually causing the danger of explosion and combustion. Thus, after the start of the temperature elevation, the molecular oxygen-containing gas is supplied in such a manner that the easily polymerizing compound gas composition exceeds the concentration of the upper explosion limits. The term "the concentration of the upper explosion limits of an easily polymerizing compound gas" as used herein means the numerical value which is fixed by the concentration of the easily polymerizing compound and the volumetric ratio (%) of the molecular oxygen-containing gas in the interior of the column. As another example, the explosion limits of methacrylic acid are illustrated in FIG. 3. The concentration in the upper explosion limits can be found by the use of an explosion limits measuring device of the type designated by the Mining Bureau of America or an explosion limits measuring device of the type proposed by Kitagawa Research Laboratory.

For the supply of the molecular oxygen-containing gas, any of the known methods may be adopted. For example, the gas may be directly incorporated by bubbling into the bottom liquid of the column or it may be indirectly incorporated after being dissolved in a solvent. The bubbling can be easily attained by supplying the molecular oxygen-containing gas in the form of a gas via the bottom of the distilling column and/or the reboiler.

The site for the supply of the molecular oxygen-containing gas does not need to be limited particularly. The molecular oxygen-containing gas may be supplied directly into the bottom of the distilling column. It may be otherwise supplied from the condenser or the reboiler or may be indirectly added in the form of a solution in a proper solvent. Incidentally, the supply of the molecular oxygen-containing gas through the reboiler is particularly advantageous because this supply is capable of particularly effectively preventing the polymerization in the interior of the reboiler. As the molecular oxygen-containing gas, air can be used besides the oxygen gas.

The method for elevating the temperature of the distilling column does not need to be particularly discriminated. Any of the known methods may be adopted for the elevation of the temperature. For example, the temperature elevation can be attained by supplying steam, hot water, or warm water to the reboiler which is connected to the bottom of the column. The easily copolymerizing compound-containing solution as the liquid raw material is gradually supplied after the polymerization inhibitor has been added to the bottom liquid of the distilling column having a temperature of not higher than 80° C. and the temperature elevation of the column has been started. The solution thus supplied has added thereto the polymerization inhibitor at a prescribed concentration similarly in the conventional procedure. By continuing the supply of the solution which has contained therein the polymerization inhibitor prior to the supply of the heat source till the stationary state is assumed, more effective prevention of the polymerization can be attained.

This invention prefers to circulate the bottom liquid of the distilling column to the column prior to starting the temperature elevation of the column as shown FIG. 1, for example. This circulation can be fulfilled by causing the bottom liquid of the column to be joined with the circulating liquid R in the middle stage of the column, at a feed orifice (2), or further at a reboiler (4) through the medium of a pump (5) and advanced in the interior of the column. The site for this circulation may be the top of the column, the middle stage of the column, or the bottom of the column, whichever fits the occasion best. The circulation to the top of the column, among other sites mentioned above, proves particularly effective. Since this circulation of the bottom liquid of the column allows effective utilization of the polymerization inhibitor, the polymerization due to the condensation of the easily polymerizing compound gasified during the course of the temperature elevation can be prevented and, at the same time, the prevention of the polymerization due to the decrease of the duration of the temperature elevation and the decrease of the amount of the heat source to be supplied can be promoted.

Now, the method of this invention for starting up the distilling column will be explained below with FIG. 1, FIG. 2, and FIG. 4 by citing, for example, the case of obtaining an acrylic acid-containing gas by the reaction of catalytic gas phase oxidation of propylene, propane, or acrolein, giving the gas a counterflow wash and extraction with a heavy crude acrylic acid collecting liquid thereby obtaining an acrylic acid-containing solution, and distilling this solution and removing water and low boiling compounds from the acrylic acid contained in the solution and the case of removing high boiling compounds from acrylic acid.

The removal of water and low boiling impurities from the acrylic acid-containing solution is generally implemented by the use of an azeotropic solvent. Then, the distillation is generally carried out under normal pressure, under a reduced pressure, or preferably under an operating pressure in the range of 100–1013 hPa absolute at a bottom temperature in the range of 60–120° C.

The composition of the acrylic acid-containing solution cannot be impartially defined because it is variable with the operating conditions of the component steps of the process. It may comprise 50–80 wt. % of acrylic acid, 1–10 wt. % of acetic acid, 10–30 wt. % of water, and 1–10 wt. % of the other components such as acrolein, formaldehyde, maleic anhydride, furfural, benzaldehyde, and acrylic acid dimer, for example. The can liquid obtained in the column in consequence of the purification is composed of 90–99 wt. % of acrylic acid, 0.01–5.0 wt. % of acetic acid, 1–1000 wt. ppm of water, and 0.5–10 wt. % of other components such as maleic anhydride, furfural, benzaldehyde, and acrylic acid dimer.

First, the liquid equivalent to the can liquid is introduced into a distilling column (1) via a feed orifice (2) as illustrated in FIG. 1 and labeled as "initial liquid." The amount of the liquid thus introduced is generally 1–5 times, preferably 1–2 times, and particularly preferably 1–1.5 times the amount of the bottom liquid. The polymerization inhibitor concentration of the bottom liquid in the distilling column (1) in the stationary state is generally in the range of 0.01–1.0 wt. %. Thus, the polymerization inhibitor is supplied to the bottom of the column in such a manner that the polymerization inhibitor concentration in the bottom liquid of the column will be in the range of 0.01–10 wt. %, preferably 0.01–2 wt. %, and particularly preferably 0.01–1.5 wt. %. The polymerization inhibitor is supplied so that the bottom temperature of the column will be not higher than 80° C., preferably not higher than 50° C., and particularly preferably not higher than 30° C. Incidentally, the amount of the bottom liquid is varied with the amount of production and the purpose of separation.

Subsequently, the azeotropic solvent-containing solution having the polymerization inhibitor charged therein in advance is supplied to the condenser (4) attached to the distilling column (1) and circulated therein. This circulation of the solution is continued till the whole internal area of the condenser (4) assumes a wetted state. As a result, the polymerization which is generated during the condensation of the gas can be prevented even when the easily polymerizing compound-containing gas is supplied into the condenser (4). Further, since the reflux liquid is supplied through the top of the column, the interior of the column assumes the state wetted with the reflux liquid and the polymerization generated during the condensation of the gas is prevented. When the circulating liquid contains the azeotropic solvent, then the circulating liquid from the condenser (4) can be separated into an azeotropic solvent phase and a water phase. Thus, the water phase may be removed from the circulating liquid and only the azeotropic solvent may be circulated as illustrated in FIG. 1.

Then, the inert gas and/or the molecular oxygen-containing gas is supplied to the distilling column (1) via the top of the column or the bottom thereof so as to adjust the molecular oxygen-containing gas concentration in the distilling column (1) in the range of 0.1–9 vol. %. This molecular oxygen-containing gas concentration corresponds to the position of ① in FIG. 2.

Then, the operating pressure is adjusted so that the pressure in the top of the distilling column will be in the range of 100–1013 hPa absolute.

After the interior of the column has been confirmed to suffer from no leakage of gas, the easily polymerizing compound-containing solution may be supplied to the distilling column (1) via the feed orifice (2) and then added to the initial liquid. Since the amount of the bottom liquid of the column is variable with the amount of production and the purpose of separation, the polymerization inhibitor is supplied to the bottom liquid of the column till the polymerization inhibitor concentration in the bottom liquid will be in the range of 0.1–10 wt. %.

The circulating liquid may be supplied prior to the temperature elevation to the condenser (4) which is attached to the top of the distilling column (1) to start the circulation of the liquid and the circulating liquid may be refluxed from the top of the distilling column (1) or the bottom liquid of the column may be supplied into the interior of the distilling column (1) through the pump (5). By this refluxing operation, the interior of the distilling column (1) can be wetted with the circulating liquid and prevented from polymerization.

Then, the reboiler (3) is supplied with steam to elevate the temperature inside the distilling column (1). After the start of the temperature elevation inside the distilling column (1) has been confirmed, the easily polymerizing compound-containing solution is continuously supplied through the feed orifice (2) and the solution having an azeotropic solvent as a main component through the top of the column. The easily polymerizing compound-containing solution is the same as that which is supplied in the stationary state. The polymerization inhibitor concentration in the feed raw material, however, cannot be impartially specified because it is variable with the purpose of separation and the ratio of concentration.

During the course of the temperature elevation, the molecular oxygen-containing gas is supplied at such a ratio that the easily polymerizing compound-containing gas composition in the column exceeds the concentration in the upper explosion limits. That is, the molecular oxygen-containing gas is supplied when the temperature of the top of the column begins to rise. The amount of the gas to be supplied is preferred to be in the range of 0.01–5 vol. %, relative to the vapor flow rate of the easily polymerizing compound generated in the distilling column (1). The oxygen concentration at a temperature of 50° C. is increased from 5 vol. % to 40 vol. %, for example. The relation between the acrylic acid concentration and the oxygen concentration in the distilling column is illustrated in type specimen in FIG. 2. The composition during the course of the temperature elevation is represented by ② in FIG. 2, for example and the composition exceeding the concentration in the upper explosion limits at a temperature of 50° C. is represented by ③ in FIG. 2, for example.

Then, the amount of the feed material and the amount of the reflux liquid are gradually increased to their respectively prescribed levels. The extraction of the distillate is started after the amount of the distillate to the condenser (4) has begun to increase. When the water and the low boiling substance contained in acrylic acid are separated, the extraction of the bottom liquid of the column is started generally at the time that the temperature of the bottom of the column has reached a level in the range of 60–120° C.

In this invention, the bottom liquid of the column is preferred to be supplied as the reflux liquid to the middle stage of the distilling column (1) via the pump (5) or to be joined to part of the reflux liquid in the condenser (4) or to be circulated inside the column via the feed orifice (2). This refluxing operation is preferred because it enables the interior of the distilling column (1) to be wetted with the refluxing liquid and prevents the polymerization which is generated during the condensation of the gas. The term "middle state of the column" refers to such parts in the plate tower or the packed tower as mounts a packing material or perform actual separation and purification and, in the absence of such a packing material, means the middle part of the distilling column excepting the bottom part and the top part of the column. As the method for refluxing the liquid to the middle stage of the column, therefore, the circulation from the feed stage is conceivable besides the provision of a separate circulating orifice at the middle stage of the column.

Now, the method for removing high boiling impurities from the acrylic acid will be explained below with reference to FIG. 4. First, the removal of the high boiling impurities from the acrylic acid is generally effected by the use of a high boiling separating column. This operation is properly carried out by distilling the acrylic acid-containing solution generally under a reduced pressure, preferably under an operating pressure in the range of 10–150 hPa absolute at a column bottom temperature in the range of 60–120° C.

The composition of the acrylic acid-containing solution cannot be impartially specified because it varies with the operating conditions of the component steps of the process. It comprises 90–99 wt. % of acrylic acid, 1–1000 wt. ppm of acetic acid, 1–1000 wt. ppm of water, and a total of 1–10 wt. % of the other components such as acrolein, formaldehyde, maleic anhydride, furfural, benzaldehyde, and acrylic acid dimer, for example. The acrylic acid-containing solution mentioned above is supplied to the distilling column (1) through the feed orifice (2) and labeled as "the initial liquid." The amount of this solution to be supplied is generally 1–5 times, preferably 1–2 times, and particularly preferably 1–1.5 times, the amount of the bottom liquid of the column. The polymerization inhibitor concentration in the bottom liquid of the distilling column (1) in the stationary state is generally in the range of 1–15 wt. %. Thus, the polymerization inhibitor is supplied to the bottom liquid of the column in such a manner that the polymerization inhibitor concentration in the bottom liquid will be in the range of 1–50 wt. %, preferably 1–30 wt. %, and particularly preferably 1–23 wt. %. The polymerization inhibitor is so supplied to the bottom part of the column that the temperature of the bottom of the column will be not higher than 80° C., preferably not higher than 50° C., and particularly preferably not higher than 30° C.

Then, the acrylic acid-containing solution mentioned above which has contained a polymerization inhibitor in advance is supplied to the condenser attached to the distilling column (1) to start the circulation similarly to the removal of the water and the low boiling impurities from the acrylic acid-containing solution mentioned above. The circulation of the solution is continued till the entire internal area of the condenser is wetted with the solution. This circulation, therefore, can prevent the polymerization which occurs during the condensation of the gas even when the easily polymerizing compound is supplied into the condenser.

The inert gas and/or the molecular oxygen-containing gas is supplied to the distilling column (1) through the top or the bottom of the column in such a manner that the molecular oxygen-containing gas concentration in the distilling column (1) will be adjusted in the range of 0.1–9 vol. %. This molecular oxygen-containing gas corresponds to the position ① in FIG. 2.

Then, the operating pressure is adjusted so that the pressure in the top of the distilling column will be in the range of 10–150 hPa absolute.

After the interior of the column has been confirmed to suffer from no leakage of gas, the easily polymerizing compound-containing solution may be supplied to the distilling column (1) via the feed orifice (2) and then added to the initial liquid. Since the amount of the bottom liquid of the column is variable with the amount of production and the purpose of separation, the polymerization inhibitor is supplied to the column till the polymerization inhibitor concentration in the bottom liquid of the column will be in the range of 0.1–50 wt. %.

Then, the circulating liquid is supplied prior to the temperature elevation to the condenser (4) attached to the top part of the distilling column (1) to start the circulation of the liquid. Otherwise, the circulating liquid may be refluxed from the top of the distilling column (1) or the bottom liquid of the column may be supplied to the interior of the distilling column (1) through the pump (5). This refluxing operation is commendable because it enables the interior of the distilling column (1) to be wetted with the refluxing liquid and consequently prevented from the polymerization.

Then, the temperature in the distilling column (1) is elevated by supplying the reboiler (3) with steam. After the start of the temperature elevation has been confirmed in the distilling column (1), the refluxing liquid of the condenser (3) is circulated to effect a total reflux operation.

During the course of the temperature elevation, the molecular oxygen-containing gas is so supplied that the easily polymerizing compound gas composition in the column will exceed the concentration in the upper explosion limits. That is, the molecular oxygen-containing gas is supplied when the temperature in the top of the column begins to rise. The amount of the gas so supplied is preferred to be in the range of 0.01–5 vol. % based on the vapor flow rate of the easily polymerizing compound generated in the distilling compound (1). The oxygen concentration at a temperature of 50° C. is increased from 5 vol. % to 40 vol. %, for example.

The relation between the acrylic acid concentration and the oxygen concentration in the distilling column is illustrated in type section in FIG. 2. The composition during the course of the temperature elevation, for example, corresponds to the position ② in FIG. 2 and the composition exceeding the concentration in the upper explosion limits at a temperature of 50° C., for example, corresponds to the position of ③ in FIG. 2.

Then, after the total reflux operation has been stabilized, the easily polymerizing compound-containing solution is continuously supplied through the feed orifice (2). The easily polymerizing compound-containing solution mentioned above is the same as the solution supplied in the stationary state. Incidentally, the polymerization inhibitor concentration in the feed material cannot be impartially specified because it is variable with the purpose of separation and the ratio of concentration.

Then, after the amount of the distillate into the condenser has begun to increase, the extraction of the distillate is started. When the high boiling substances contained in the acrylic acid are separated, the extraction of the bottom liquid of the column is started at the time that the temperature of the bottom part of the column generally surpasses a level in the range of 60–120° C., though variable with the kind of the substances to be separated by distillation or the boiling point.

The method of this invention for starting up the distilling column can be applied similarly when the bottom liquid of the distilling column which has been made to reach the stationary operation by the method for starting up the distilling column mentioned above is further distilled. Specifically, the bottom liquid of the distilling column is fed as the initial liquid to the distilling column of the next step and it is then made to add the polymerization inhibitor. In this respect, though the bottom liquid of the first distilling column has already contained the polymerization inhibitor therein, it is generally required further to incorporate the polymerization inhibitor therein.

In the process for the production of the easily polymerizing compound, since the target product tends to polymerize, the removal of the water and the low boiling substances by distillation and the removal of the high boiling substance by distillation are carried out sequentially in the order mentioned in the process for the purification. Further, the concentration of the target compound supplied to the distilling column is heightened in accordance as the process of distillation advances. Thus, the concentration of the polymerization inhibitor is heightened in the sequential steps of the process for distillation. When the bottom liquid of the first distilling column is supplied as the initial liquid for the second distilling column, therefore, it has acquired a lower polymerization inhibitor concentration than in the bottom liquid of the second distilling column in the stationary state.

The distilling column as described above has handled the acrylic acid-containing solution. This description applies similarly to the distilling column which is operated to obtain methacrylic acid-containing gas by changing the feed gas to the reaction vessel, collect this gas in a collecting liquid, and distill the methacrylic acid-containing solution consequently collected.

It is further applicable similarly to the distilling column which is operated to distill a (meth)acrylic ester in the production of the (meth)acrylic ester.

This invention provides a method of exceptionally high economic value which prevents the polymerization during the course of starting up the distilling column, infallibly avoids the explosion and the combustion, and permits a stable start of the distilling column.

EXAMPLES

Now, this invention will be described more specifically below with reference to working examples.

Example 1

Figure 4:
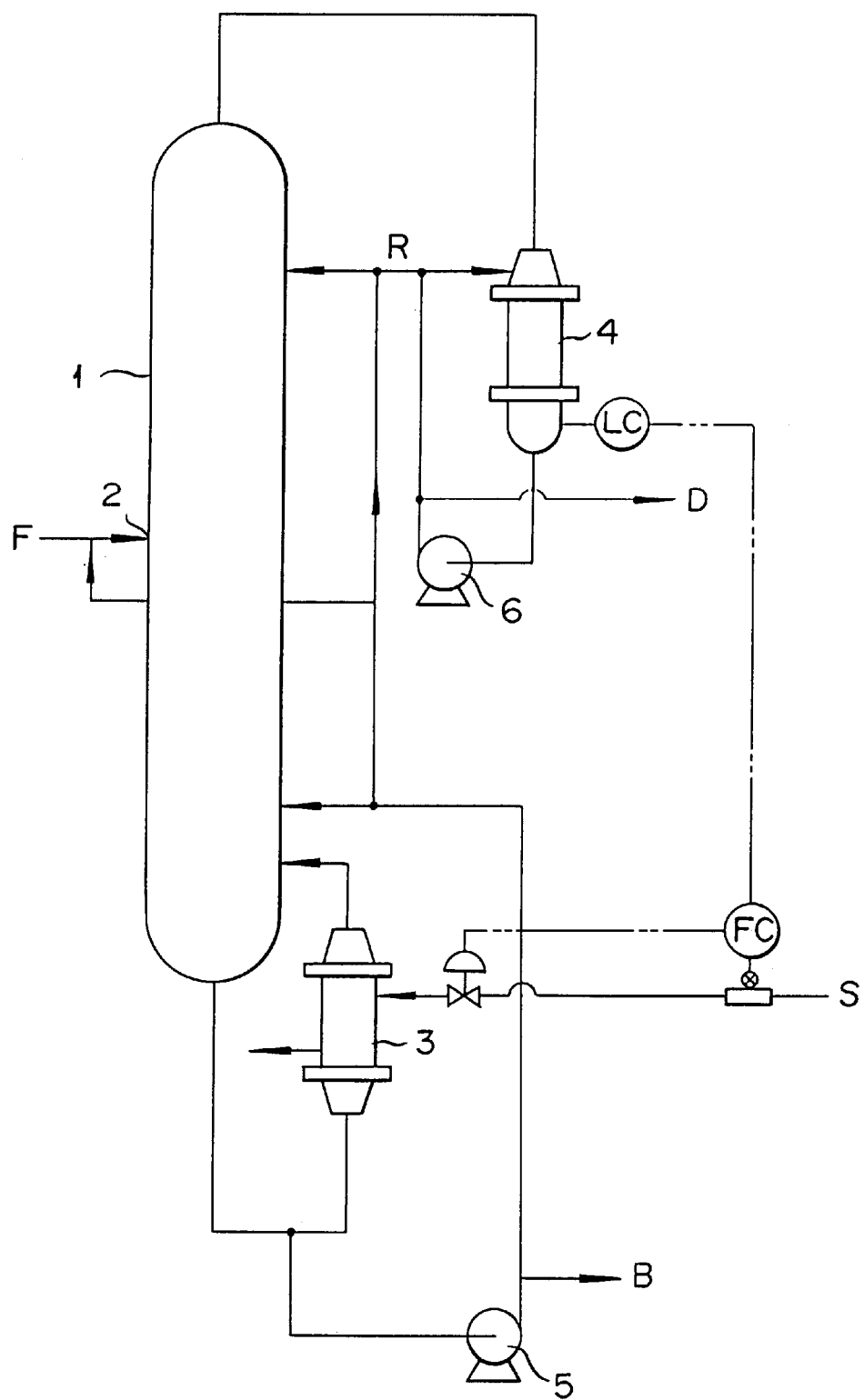
FIG. 4 is a diagram illustrating the flow of a liquid during the operation of starting up a distilling column according to this invention where the reflux liquid from a condenser is wholly put to refluxation.
Figure 5:
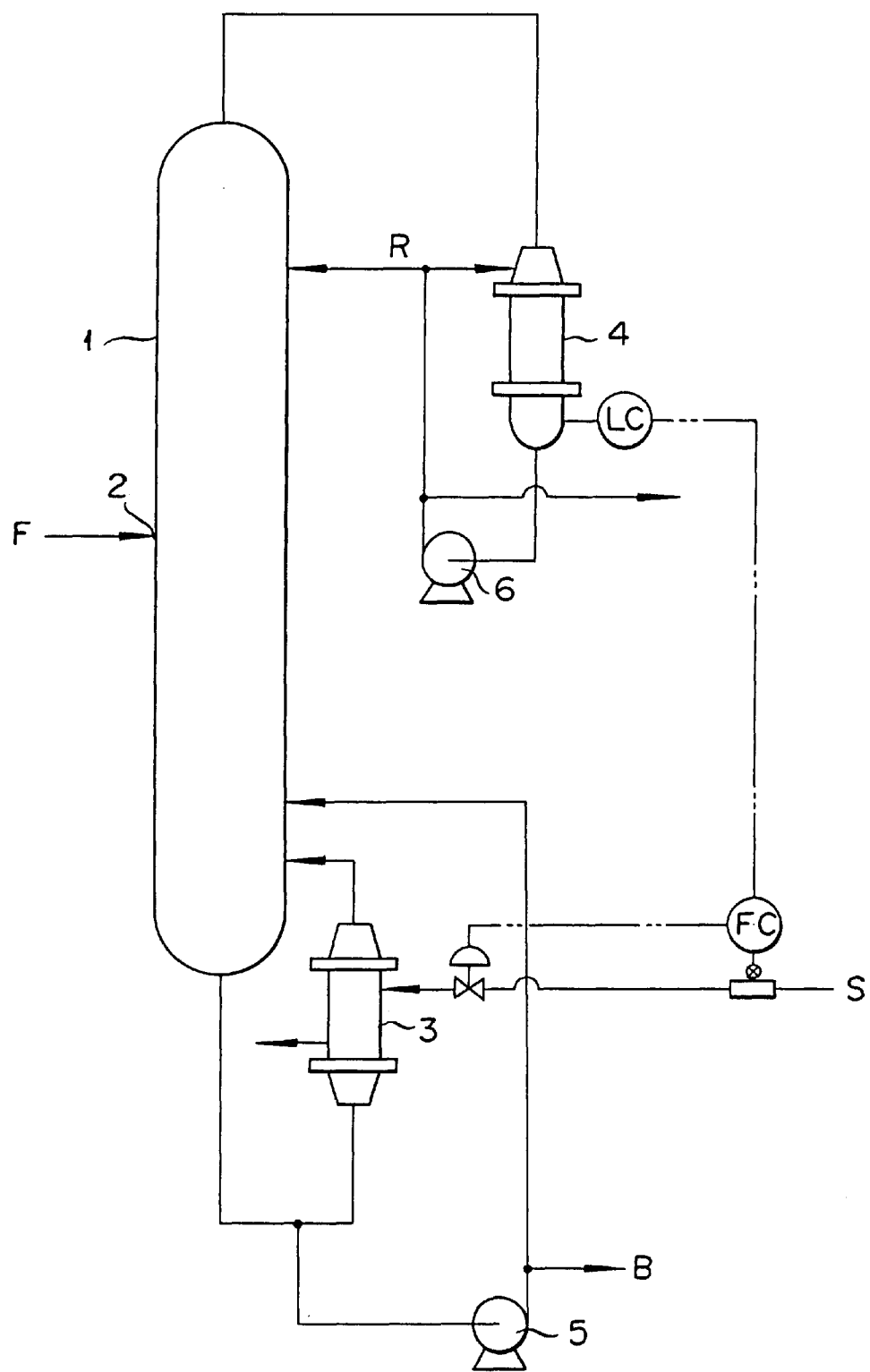
FIG. 5 is a diagram illustrating the flow of a liquid during the conventional operation of starting up the distilling column.

A distilling column furnished therein with 50 stepped sieve trays made of stainless steel (SUS 316) and measuring 1500 mm in inside diameter as illustrated in FIG. 4 was used. The column was provided in the top part thereof with an output port and a reflux liquid inlet pipe, in the central part thereof with an inlet pipe for admitting the liquid feed (raw material) to be treated, and in the bottom part thereof with a circulation pipe for circulating the liquid feed, a transfer pipe leading to the next step, a liquid feed pump, and a strainer. The distilling column was provided in the bottom part thereof with a reboiler (the vertical shell-and-tube type) adapted to pass a given fluid on the tubes side by means of spontaneous circulation.

The distilling column was started up by the following method. It was provided, however, that the vapor flow rate of acrylic acid generated in the distilling column during the normal operation was set at about 5000 kg/h, the reflux ratio, R/D, at 0.5, and the ratio of concentration, F/B, at 5.

(a) The molecular oxygen-containing gas concentration in the column was set at 7 vol. %.

(b) The pressure in the top of the column was set at 47 hPa.

(c) To the bottom of the column, 5 $m^3$ of the fluid was supplied and 50 kg of phenothiazine (PTZ) was supplied as well. The total polymerization inhibitor (PTZ) concentration in the column was 1 wt % based on the weight of the bottom liquid and the fluid was composed of 98 wt. % of acrylic acid and 2 wt. % of acrylic acid dimer.

(d) The temperature elevation of the column was started by supplying steam to the reboiler.

(e) The load on the reflux liquid was raised to the set level of 1667 kg/h to effect a total reflux operation.

(h) The feed liquid was supplied after the stabilization of the total reflux operation was confirmed. This feed liquid was made to contain phenothiazine in a concentration of 0.2 wt. %.

(i) The extraction of the distillate was started when the amount of the distillate began to increase.

(j) The extraction of the bottom liquid of the column was started when the temperature of the bottom part of the column rose above the set level of 90° C.

(k) The relevant fluids were supplied till their respectively prescribed levels (4167 kg/h of the feed liquid, 1667 kg/h or reflux liquid, 3334 kg/h or distillate, and 833 kg/h of extract from the bottom of the column).

(i) The molecular oxygen-containing gas was supplied at a feed volume of 10 $Nm^3/h$ to effect the normal operation.

During the operation of starting up the distilling column mentioned above, the temperature in the column and the pressure in the column showed no abnormality and remained in the stable state. When the distilling column was stopped to inspect the interior, slight adhesion of a polymer was detected in the strainers disposed in the bottom part of the column. About 0.5 kg of polymer was detected on the trays inside the column. No polymer was detected in the bottom part of the column, in the pump, or in the reboiler, etc. The polymer was removed by an operation of cleaning. The results are shown in Table 1. The results shown in Table 1 were determined on the three-point scale, wherein:

○: No problem found at the time of starting up the distilling column. There boiler was not blocked when the total amount of polymer was not more than 1 kg.

Δ: During the operation of starting up the distilling column, the operation was obtained in spite of the upward trends of the temperature/pressure in the bottom part of the column. The reboiler was clogged when the total amount of polymer was less than 15 kg.

X: During the operation of starting up the distilling column, the operation was not obtained because of the upward trends of the temperature/pressure in the bottom part of the column. The reboiler was clogged when the total amount of polymer was not less than 15 kg.

Example 2

The operation of starting up the distilling column was performed by following the procedure of Example 1 while supplying 50 kg of phenothiazine at a bottom temperature of 45° C. (ambient temperature of 20° C.).

During the operation of starting up the distilling column, the operation retained a substantially stable state in spite of slight increases of the temperature in the bottom of the column and the pressure in the bottom. When the distilling column was stopped and the interior of the column was inspected, about 2 kg of polymer was detected in the strainers, about 3 kg of polymer in the bottom of the column and on the trays, and a slight amount of polymer in the pump. In the reboiler, one of a total of 300 tubes was clogged. The polymer was removed by washing. The results are shown in Table 1.

Example 3

The operation of starting up the distilling column was performed by following the procedure of Example 2 while supplying 25 kg of phenothiazine to the column at a bottom temperature of 45° C. (ambient temperature of 20° C.). Incidentally, the polymerization inhibitor concentration in the stationary state was 1 wt. %.

During the operation of starting up the distilling column, the operation retained a substantially stable state in spite of increases of the temperature in the bottom of the column and the pressure in the bottom and a slight fluctuation of the discharging pressure of the pump. When the distilling column was stopped and the interior of the column was inspected, about 5 kg of polymer was detected in the strainers, about 3 kg of polymer in the bottom of the column, about 5 kg of polymer on the trays, and a slight amount of polymer in the pump. In the reboiler, three of a total of 300 tubes were clogged. The polymer was removed by washing. The results are shown in Table 1.

Example 4

The operation of starting up the distilling column was performed by following the procedure of Example 1 while supplying the molecular oxygen-containing gas at a column top temperature of 50° C. at a feed volume of 10 Nm$^3$/h.

During the operation of starting up the distilling column, the temperature in the column and the pressure in the column showed no abnormality, no polymer was found in the strainers, and a polymer was slightly detected on the trays. No polymer was detected in the bottom of the column, in the pump, or in the reboiler. The polymer was removed by a washing operation. The results are shown in Table 1.

Example 5

The operation of starting up the distilling column was performed by following the procedure of Example 1 while supplying the reflux liquid at a flow rate of 1667 kg/h prior to the supply of steam.

During the operation of starting up the distilling column, the operation was retained in a stable state and the temperature in the column and the pressure in the column showed absolutely no sign of abnormality. When the operation of the distilling column was stopped and the interior of the column was inspected, no polymer was found in the strainers and a polymer was slightly detected on the trays. No polymer was detected in the bottom of the column, in the pump, or in the reboiler. The polymer was removed by a washing operation. The results are shown in Table 1.

Comparative Example 1

The operation of starting up the distilling column was performed by following the procedure of Example 1 while supplying the initial liquid alone and omitting the supply of phenothiazine.

After the temperature elevation of the interior of the column was started, the temperature in the bottom and the pressure in the bottom were increased so much as to induce cavitation and bring a forced stop of the pump. When the interior of the column was inspected, a large amount of polymer was detected in the strainers. About 10 kg of polymer was detected in the bottom of the column and on the trays and a large amount of polymer was detected in the pump. In the reboiler, 10 of a total of 300 tubes were clogged. Though the polymer was removed by a washing treatment, the treatment required a long time. Part of the polymer could not be easily removed with a detergent and had to be removed by chipping. The cavitation inflicted damage on the impellers. The results are shown in Table 1.

Comparative Example 2

The operation of starting up the distilling column was performed by following the procedure of Example 4 while supplying only the initial liquid and omitting the supply of phenothiazine.

After the temperature elevation of the interior of the column was started, the temperature in the bottom and the pressure in the bottom were increased so much as to induce cavitation and bring a forced stop of the pump. When the interior of the column was inspected, a large amount of polymer was detected in the strainers. About 8 kg of polymer was detected in the bottom of the column and on the trays and a large amount of polymer was detected in the pump. In the reboiler, 8 of a total of 300 tubes were clogged. Though the polymer was removed by a washing treatment, the treatment required a long time. Part of the polymer could not be easily removed with a detergent and had to be removed by chipping. The cavitation inflicted damage on the impellers. The results are shown in Table 1.

Comparative Example 3

The operation of starting up the distilling column was performed by repeating the procedure of Example 5 while supplying only the initial liquid and omitting the supply of phenothiazine.

After the temperature elevation of the interior of the column was started, the temperature in the bottom and the pressure in the bottom were increased so much as to induce cavitation and bring a forced stop of the pump. When the interior of the column was inspected, a large amount of polymer was detected in the strainers. About 5 kg of polymer was detected in the bottom of the column and on the trays and a large amount of polymer was detected in the pump. In the reboiler, 5 of a total of 300 tubes were clogged. Though the polymer was removed by a washing treatment, the treatment required a long time. The results are shown in Table 1.

Example 6

A distilling column furnished therein with 50 stepped sieve trays made of stainless steel (SUS 316) and measuring 1500 mm in inside diameter as illustrated in FIG. 1 was used. The column was provided in the top part thereof with an output port and a reflux liquid inlet pipe, in the central part thereof with an inlet pipe for admitting the liquid feed to be treated, and in the bottom part thereof with a circulation pipe for circulating the liquid feed, a transfer pipe leading to the next step, a liquid feed pump, and a strainer. The distilling column was provided in the bottom part thereof with a reboiler (the vertical shell-and-tube type) adapted to pass a given fluid on the tubes' side by means of spontaneous circulation.

The distilling column was started up by the following method. It was provided, however, that the vapor flow rate of acrylic acid generated in the distilling column during the normal operation was set at about 7000 kg/h, the reflux ratio, R/D, at 5, and the ratio of concentration, F/B, at 1.5. Methyl isobutyl ketone was used (MIBK) as an azeotropic solvent. The feed liquid was composed of 70 wt. % of acrylic acid, 20 wt. % of water, and 10 wt. % of acetic acid.

(a) The molecular oxygen-containing gas concentration in the column was set at 7 vol. %.

(b) The pressure in the top of the column was set at 150 hPa.

(c) To the bottom of the column, 5 m³ of the fluid was supplied and 5 kg of phenothiazine (PTZ) was supplied as well. The total polymerization inhibitor (PTZ) concentration in the column was 0.1 wt. % based on the weight of the bottom liquid and the fluid was composed of 98 wt. % of acrylic acid and 2 wt. % of acetic acid.

(d) The bottom liquid was supplied through the feed orifice to effect the circulation of the liquid at a flow rate of 1000 kg/h.

(e) The temperature elevation of the column was started by supplying steam to the reboiler.

(f) As the temperature in the column began to rise, the feed liquid and there flux liquid formed mainly of an azeotropic solvent were supplied. The feed liquid contained 0.03 wt. % of phenothiazine and the reflux liquid contained phenothiazine in a concentration of 0.022 wt. %.

(g) The feed liquid and the reflux fluid were supplied till their respectively prescribed levels of 2500 kg/h and 4167 kg/h.

(h) As the amount of the distillate began to increase, the extraction of the distillate was started. The distillate was separated into an azeotropic solvent phase and a water phase. The azeotropic solvent phase alone was circulated and put to use.

(i) The extraction of the bottom liquid of the column was started when the temperature of the bottom of the column rose above the set level of 100° C.

(j) The relevant fluids were supplied till their respectively prescribed levels (2500 kg/h of feed liquid, 4167 kg/h or reflux liquid, 833 kg/h or distillate, and 1667 kg/h of extract from the bottom of the column).

(k) The molecular oxygen-containing gas was supplied at a feed volume of 10 NM³/h to effect the normal operation.

During the operation of starting up the distilling column mentioned above, the temperature in the column and the pressure in the column showed no abnormality and remained in the stable state. When the distilling column was stopped to inspect the interior, slight adhesion of a polymer was detected in the strainers disposed in the bottom part of the column. Only a small amount of polymer was detected on the trays inside the column. No polymer was detected in the bottom of the column, in the pump, or in the reboiler. The polymer was removed by a cleaning operation. The results are shown in Table 1.

Comparative Example 4

The operation of starting up the distilling column was performed by repeating the procedure of Example 6 while supplying only the initial liquid and omitting the supply of phenothiazine.

After the temperature in the column began to rise, the temperature in the bottom of the column and the pressure in the bottom increased so much as to induce cavitation and bring a forced stop of the pump. When the interior of the column was inspected, a large amount of polymer was detected in the strainers. About 8 kg of polymer was detected in the bottom of the column and on the trays and a large amount of polymer was detected in the pump. In the reboiler, 5 of a total of 300 tubes were clogged. Though the polymer was removed by a cleaning treatment, the treatment consumed much time. The results are shown in Table 1.

TABLE

| | Example | | | | | | Comparative Example | | | |
|---|---|---|---|---|---|---|---|---|---|---|
| | 1 | 2 | 3 | 4 | 5 | 6 | 1 | 2 | 3 | 4 |
| DISTILLING COLUMN CONDITION | | | | | | | | | | |
| Press. in the top (hPa) | 47 | 47 | 47 | 47 | 47 | 150 | 47 | 47 | 47 | 150 |
| Temp. in the top (° C.) | 63 | 63 | 63 | 63 | 63 | 46 | 63 | 63 | 63 | 46 |
| Temp. in the bottom (° C.) | 90 | 90 | 90 | 90 | 90 | 100 | 90 | 90 | 90 | 100 |
| Reflux ratio, R/D | 0.5 | 0.5 | 0.5 | 0.5 | 0.5 | 5 | 0.5 | 0.5 | 0.5 | 5 |
| Ratio of conc., F/B | 5 | 5 | 5 | 5 | 5 | 1.5 | 5 | 5 | 5 | 1.5 |
| Vapor flow rate of acrylic acid (kg/h) | 5000 | 5000 | 5000 | 5000 | 5000 | 7000 | 5000 | 5000 | 5000 | 7000 |
| Feed (kg/h) | 4167 | 4167 | 4167 | 4167 | 4167 | 2500 | 4167 | 4167 | 4167 | 2500 |
| Reflux liquid (kg/h) | 1667 | 1667 | 1667 | 1667 | 1667 | 4167 | 1667 | 1667 | 1667 | 4167 |
| Extraction of bottom liquid (kg/h) | 833 | 833 | 833 | 833 | 833 | 1667 | 833 | 833 | 833 | 1667 |
| Concentration Of PTZ in column (wt. %) | 1 | 1 | 1 | 1 | 1 | 0.1 | 1 | 1 | 1 | 0.1 |
| Conc. of oxygen cont. gas (Nm³/h) | 10 | 10 | 10 | 10 | 10 | 10 | 10 | 10 | 10 | 10 |
| Conc. of Oxygen gas (vol. %) | 0.64 | 0.64 | 0.64 | 0.64 | 0.64 | 0.46 | 0.64 | 0.64 | 0.64 | 0.46 |
| azeotropic solvent | | | | | | MIBK** | | | | MIBK** |
| STARTING CONDITION | | | | | | | | | | |
| Conc. of Oxygen gas in column (vol. %) | 7 | 7 | 7 | 7 | 7 | 7 | 7 | 7 | 7 | 7 |
| Press. of top of column (hpa) | 47 | 47 | 47 | 47 | 47 | 150 | 47 | 47 | 47 | 150 |
| Amount of bottom liquid (m³) | 5 | 5 | 5 | 5 | 5 | 5 | 5 | 5 | 5 | 5 |
| Composition of | | | | | | | | | | |

TABLE-continued

|  | Example | | | | | | Comparative Example | | | |
|---|---|---|---|---|---|---|---|---|---|---|
|  | 1 | 2 | 3 | 4 | 5 | 6 | 1 | 2 | 3 | 4 |
| bottom liquid | | | | | | | | | | |
| acrylic acid (wt. %) | 98 | 98 | 98 | 98 | 98 | 98 | 98 | 98 | 98 | 98 |
| acrylic acid (wt. %) | 2 (dimer) | 2 (dimer) | 2 (dimer) | 2 (dimer) | 2 (dimer) | 2 (acetic acid) | 2 (dimer) | 2 (dimer) | 2 (dimer) | 2 (acetic acid) |
| Amount. of PTZ in bottom liquid (kg) | 50 | 50 | 25 | 50 | 50 | 5 | 0 | 0 | 0 | 0 |
| Conc. (wt. %) of PTZ in bottom liquid | 1 | 1 | 0.5 | 1 | 1 | 0.1 | 0 | 0 | 0 | 0 |
| Introducing time of PTZ | before starting temp. elevation | at 45° C. in the bottom | at 45° C. in the bottom | before starting temp. elevation | before starting temp. elevation | before starting temp. elevation | — | — | — | — |
| Comp. of feed liquid | | | | | | | | | | |
| acrylic acid (wt. %) | 98 | 98 | 98 | 98 | 98 | 70 | 98 | 98 | 98 | 70 |
| acrylic acid (wt. %) | 2(dimer) | 2(dimer) | 2(dimer) | 2(dimer) | 2(dimer) | 10 (acetic acid) | 2 (dimer) | 2 (dimer) | 2 (dimer) | 10 (acetic acid) |
| Other (wt. %) |  |  |  |  |  | 20 (water) |  |  |  | 20 (water) |
| Introduction time of reflux liquid | after starting temp. elevation | after starting temp. elevation | after starting temp. elevation | after starting temp. elevation | before starting temp. elevation | after starting temp. elevation | after starting temp. elevation | after starting temp. elevation | before starting temp. elevation | after starting temp. elevation |
| Introduction Time of oxygen (° C.*) | 63 | 63 | 63 | 50 | 63 | 46 | 63 | 50 | 63 | 46 |
| CONDITION | | | | | | | | | | |
| Temp. and press. of column | normal | litter elevated | elevated | normal | normal | normal | elevated | elevated | elevated | elevated |
| Pump cavitation | None | None | little | None | None | None | occurred | occurred | occurred | occurred |
| Other | None | None | None | None | None | None | stop | stop | stop | stop |
| CONDITION IN COLUMN (adhesion of polymer) | | | | | | | | | | |
| Strainer | little | about 2 kg | about 5 kg | None | None | little | many | many | many | many |
| Bottom | None | about 3 kg | about 3 kg | None | None | None | about 10 kg | about 8 kg | about 5 kg | about 8 kg |
| Tray | about 0.5 kg | about 3 kg | about 5 kg | little | little | little | about 10 kg | about 8 kg | about 5 kg | about 8 kg |
| Pump | None | little | little | None | None | None | many | many | many | many |
| Number of clogged tube in a reboiler | None | 1 | 3 | None | None | None | 10 | 8 | 5 | 5 |
| Other | None | None | None | None | None | None | difficult of washing | difficult of washing | difficult of washing | difficult of washing |
| Total valuation | ○ | Δ | Δ | ○ | ○ | ○ | X | X | X | X |

*Time of introduction of oxygen shows temperature of top of column (° C.)
MIBK**: methylisobutyl-ketone

What is claimed is:

1. A method for starting up a distilling column to handle an easily polymerizing compound-containing solution, wherein a polymerization inhibitor is supplied to a bottom liquid of the distilling column having a temperature of not higher than 80° C. at the start of an operation of the distilling column, wherein an inert gas and/or a molecular oxygen-containing gas is supplied to the interior of the column prior to the start of a temperature elevation of the distilling column till the molecular oxygen-containing gas concentration in the column reaches a level in the range of 0.1–9 vol. % and then, during the course of the temperature elevation, the molecular oxygen-containing gas is supplied till an easily polymerizing compound gas composition in the column exceeds the concentration in upper explosion limits.

2. A method according to claim 1, wherein a concentration of said polymerization inhibitor is equal to or higher than the polymerization inhibitor concentration in the bottom liquid of said distilling column in a stationary state.

3. A method according to claim 1, wherein said polymerization inhibitor is supplied to the bottom liquid of said distilling column when the temperature of the bottom of the column has risen to a level within 20° C. of the ambient temperature.

4. A method according to claim 1, wherein a reflux liquid is supplied to the distilling column through the top of the column or through a middle stage of the column prior to the temperature elevation operation of the distilling column.

5. A method according to claim 1, wherein said bottom liquid of the distilling column is circulated to a middle stage of the column.

6. A method according to claim 1, wherein the easily polymerizing compound-containing solution contains at least one member selected from the group consisting of (meth)acrylic acid and esters thereof.

\* \* \* \* \*